(12) United States Patent
Smith

(10) Patent No.: US 6,655,189 B1
(45) Date of Patent: Dec. 2, 2003

(54) EXPLOSIVE EXCITATION DEVICE AND METHOD

(75) Inventor: Kevin Scott Smith, Huntersville, NC (US)

(73) Assignee: The University of North Carolina at Charlotte, Charlotte, NC (US)

( * ) Notice: Subject to any disclaimer, the term of this patent is extended or adjusted under 35 U.S.C. 154(b) by 0 days.

(21) Appl. No.: 09/551,376

(22) Filed: Apr. 18, 2000

Related U.S. Application Data

(60) Provisional application No. 60/138,808, filed on Jun. 14, 1999.

(51) Int. Cl.[7] .................................................. G01N 3/32
(52) U.S. Cl. ......................... 73/12.04; 73/167; 73/579
(58) Field of Search ............................. 73/12.04, 167, 73/579; 102/210, 231, 215; 200/61.5; 307/121; 244/3.16

(56) References Cited

U.S. PATENT DOCUMENTS

| | | | | |
|---|---|---|---|---|
| 3,750,583 A | * | 8/1973 | White et al. ............ 102/70.2 R |
| 4,638,130 A | * | 1/1987 | Grossler et al. ........... 200/61.45 |
| 4,728,057 A | * | 3/1988 | Dunne ........................ 244/3.16 |
| 5,317,914 A | * | 6/1994 | Franco, Jr. ..................... 73/167 |
| 5,565,626 A | * | 10/1996 | Davie ............................ 73/579 |
| 6,378,435 B1 | * | 4/2002 | Bai et al. ..................... 102/215 |

* cited by examiner

Primary Examiner—Edward Lefkowitz
Assistant Examiner—Octavia Davis
(74) Attorney, Agent, or Firm—Lynn E. Barber

(57) ABSTRACT

An explosive excitation device and method of use thereof for exciting a structure during dynamic measurements. The device includes an accelerometer and an explosive charge. The device is attached at one end to the structure to be excited. The explosive charge is mounted between the accelerometer and the target structure. When the explosive charge is ignited, the accelerometer is blown away from the device. Knowing the acceleration, measured by thee accelerometer, and knowing the mass of the accelerometer, the force applied to the target structure can be calculated. The information on the force of input and the resulting motion of the target structure allows calculation of the structure's dynamic characteristics.

5 Claims, 9 Drawing Sheets

EXPLOSIVE EXCITATION DEVICE AND METHOD

CROSS-REFERENCE TO RELATED APPLICATIONS

This application claims benefit of U.S. Provisional Application No. 60/138,808 filed Jun. 14, 1999.

BACKGROUND OF THE INVENTION

1. Field of the Invention

This invention relates to structural testing, and in particular, relates to a device used to excite structures during dynamic measurements.

2. Description of the Related Art

There are a number of different types of impact testing used to evaluate industrial and consumer products to determine the mechanical resonances and vibration amplitudes of the tested structures, which are indicative of the functional suitability of the structures. Such testing during the development of products, for example, cutting tools, allows detection of structural designs which are susceptible to vibrations at their mechanical resonances, and thus may be subject to failure, malfunction or safety problems. Such tests are common on products which are used at high speeds and which carry passengers, such as automobiles or aircraft. It is important that the excitement produced in the testing be easy to apply and direct, have a large enough bandwidth and a great enough force, and be well-measured.

Prior simple impact testing devices generally utilize either some type of shaker (electric and hydraulic) or an impact test hammer having a sensor portion and a striking portion for imparting a sharp, manual impact to the structure at the desired point. Shakers are fed with a time-varying signal, and are attached to the structures to be tested, and are often not convenient to use, are expensive, and require a rather high skill level in the user. Hammers are more convenient, but also require a high skill level in the user. The size of the hammer and the material in the tip control the range of excitation frequencies. For excitation of very small cutting tools, the hammer must be quite small. It is difficult to hit the small target and to hit it with the required force. Substantial training, experience, and dexterity are often required for satisfactory testing. If the target point is missed or hit at the incorrect force, there can be measurement errors. Such devices also require space for the hammer device to be swung prior to impacting the structure. For example, in the patent of Umemura et al. (U.S. Pat. No. 5,025,655), an impact test hammer has a hollow cylindrical handle with a sensor portion on one end to sense the striking force when applied to a test object, and a grip portion on the other end, which contains a circuit operatively connected to the sensor through the handle and includes a range switch, scale conversion amplifier and a wind amplifier.

In the impact testing apparatus of Garritano et al. (U.S. Pat. No. 4,640,120), a weighted dart is dropped from a prescribed height through a tubular guide to impact a test specimen when traveling at a desired velocity and level of kinetic energy. A force transducer at the tip of the dart provides impact force information as the tip penetrates the specimen. This apparatus requires that the portions of the specimen to be tested be accessible to testing from above.

In the patent of Adelman et al. (U.S. Pat. No. 4,682,490), a power-actuated instrument comprising a movable means in a housing and an electrically responsive pulse means for triggering movement of the movable means produces a single impact force of variable magnitude and electronic means for detecting the impact force delivered, including the mechanical resonances and vibration amplitudes of the structure. The disadvantage of this instrument is that in order to achieve sufficient force, the mass of the moving component must be large. In contrast, in impact testing, the mass of the "hammer" should be small in comparison to the mass of the target. This instrument is also expensive to manufacture, bulky, and requires setting the distance from the "gun" to the target using some Teflon screws.

The apparatus for non-destructive testing of Evans (U.S. Pat. No. 4,519,245) has an impactor means for impacting the surface of a material with a predetermined force, which is regulated in magnitude and duration of the force by a control means, such as a solenoid connected to a current source and sink, and a sensor for detecting the response from the material after impact and for generating a signal proportional to the amplitude and frequency of the detected response, as compared with a stored reference signal.

Impact testing is often carried out by dropping test samples from high towers or using pressurized gases. For example, the impact test apparatus of Meir (U.S. Pat. No. 4,696,182) includes a barrel containing pressurized gas and a shuttle with a bore for carrying the test sample. A trigger element causes the shuttle to accelerate toward an open end of the barrel toward a target aligned with the open end of the barrel. Again, this method is difficult to use with small structures to be tested, or with structures requiring testing of areas on multiple sides of an object.

Although the components of the invention herein are not in themselves new, the device and method herein enabling application and measurement of the force are new.

It is therefore an object of the invention to provide an inexpensive explosive excitation device and method for impact excitation that provides a controlled, broad bandwidth, high force excitation to a structure.

It is a further object of the invention to provide a device which requires less skill to use than prior impact hammers and shakers.

It is a further object of the invention to provide a device which imparts a force which can be quite large, and has an accurately controllable excitation location.

It is a further object of the invention to provide a device which utilizes explosive excitation and enables determination of the force produced by the device.

It is a further object of the invention herein to provide a device which produces an impact of wide bandwidth (containing a broad range of frequencies), in order to excite structures that have important dynamic characteristics at high frequencies.

It is a further object of the invention to provide a device which can be used to measure dynamic characteristics of machine tools, for example, to predict, improve and/or explain cutting performance; to measure structural dynamics of aerospace, automotive or many other industrial components and assemblies; to monitor machine condition; and to characterize buildings, bridges and other infrastructures.

Other objects and advantages will be more fully apparent from the following disclosure and appended claims.

SUMMARY OF THE INVENTION

The invention herein is an explosive excitation device and method of use thereof for exciting a structure during dynamic measurements. The device of the invention includes an accelerometer and an explosive charge. The device is attached at one end to the structure to be excited. The explosive charge is mounted between the accelerometer and the target structure. When the explosive charge is ignited, the accelerometer is blown away from the device. Knowing the acceleration, measured by the accelerometer, and knowing the mass of the accelerometer, the force applied to the target structure can be calculated. The information on the force of input and the resulting motion of the target structure allows calculation of the structure's dynamic characteristics.

Other objects and features of the inventions will be more fully apparent from the following disclosure and appended claims.

BRIEF DESCRIPTION OF THE DRAWINGS

FIG. 4a shows the measured hammer force (Stimulus) in Newtons (N) with time. FIG. 4b shows the measured acceleration of the target in meters/second$^2$ with time. The measurement was made using an accelerometer attached to the structure.

DETAILED DESCRIPTION OF THE INVENTION AND PREFERRED EMBODIMENTS THEREOF

The present invention is an explosive excitation device which is used for exciting a structure during dynamic measurements. The device produces a repeatable, controlled, high-bandwidth, high amplitude force to the target, and the force can be measured using an accelerometer and a knowledge of the accelerometer mass. The invention utilizes ignition of an explosive charge within or associated with the device, which in turn is attached to the structure to be tested. The explosion of the charge is followed by discharge of an accelerometer from the device at a recorded acceleration, the measurement of which, along with information on the mass of the accelerometer, enables determination of the force that excited the system.

Figure 1:
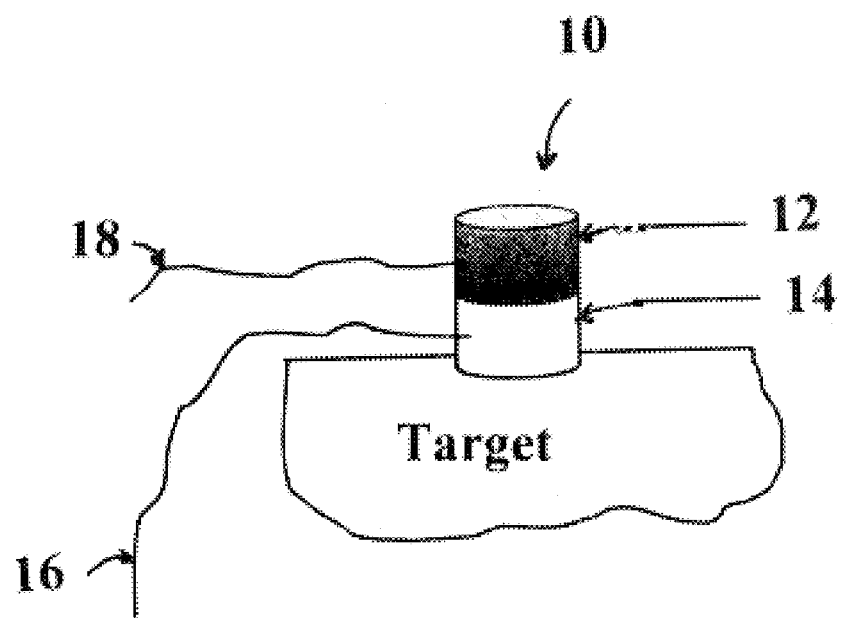
FIG. 1 is a schematic side view of one embodiment of the invention herein.

As shown in FIG. 1, the basic elements of the device 10 of the invention herein are an accelerometer 12, an explosive charge 14 positioned adjacent the accelerometer 12; an igniter 16, such as an igniter cable; and a means of measuring acceleration 18, indicated by the signal cable. In operation, when the explosive charge is ignited, the accelerometer is blown away from the device. Knowledge of the acceleration of the accelerometer and of the mass of the accelerometer enables calculation of excitation force on the structure.

An early version of the device of the invention contained the basic elements discussed above plus specific optional elements for the particular purpose of the embodiment, including an optional base attached to the an accelerometer 12 by means known in the art, for example, glue or wax. The base is not required in all embodiments of the invention, but in the embodiment shown was used to hold the components of the invention.

The accelerometer 12 may be a microelectronic device, and may be fabricated together with the charge or attached thereto by means known in the art.

Accelerometer 12 may be any accelerometer known in the art, for example, a miniature accelerometer manufactured by PCB Piezotronics (DePew, N.Y.). The size of the accelerometer would be expected to be increased for larger charges.

The location of the explosive charge 14 and the accelerometer 12 must be sufficiently close so that ignition of the charge causes the accelerometer to be blown away from the structure to which the device 10 is attached. The explosive charge 14 may be a starter pistol cap or paper cap for smaller structures, and a larger charge, for example, a blasting cap, for larger structures. The explosive charge 14 may be attached to the target, for example, with double-sided tape, hot glue or putty, or the base may remain on the structure by gravity, and to the target with mounting wax, or with other attachment means as are known in the art.

In the preferred embodiment of the invention, a range of explosive packages would be provided from which the user could select for the particular structure to be tested. It is important to have a broad bandwidth so that the impact excites a wide enough frequency range. Generally very sharp impacts excite a wide range of frequencies, but not with much energy. Wider (in time) impacts excite only lower frequencies, but with much more energy. For a hammer test, the characteristics of the impact are based on the target to be excited. Big hammers with soft tips excite structures with big masses and low frequency dynamics, and small hammers with stiff tips are used to excite small structures with high frequency dynamics. The device of the invention is particularly useful because it can produce both a sharp impact and a high force. In addition, the "shape" of the impact can be adjusted by choosing the accelerometer mass and the charge size and configuration.

An igniter 16 is used as is known in the art. For example, for small devices of the invention, an igniter could be used such as that used for model rocket engines. Any kind of spark generator, for example, as is found in a gas grill, or any kind of heat source or flame would be usable in the invention. Users of the device for different applications might prefer different igniters. In a prototype of the invention, the igniter 16 is mounted in a bore through the wall of the device, extending into the central bore wherein the explosive charge 14 is located. In this embodiment, a plug seals the bore where the accelerometer is mounted. When the explosive charge is ignited, the accelerometer is blown away from the device and its acceleration recorded. Knowledge of the acceleration and the mass of the accelerometer enables calculation of the force that excited the system. An optional plug and/or a boundary seal may be used to hold the explosive charge in place.

Briefly, to use the device of the invention, the user mounts the base of the device of the invention on the structure to be tested. The accelerometer is connected to any data acquisition system as is known in the art. The response transducers, which may be accelerometers, velocity measuring devices, or displacement transducers, are mounted and connected to the data acquisition system, such as a computer. The charge is connected to the trigger system and fired. In the prototype of the invention, the trigger system is a switch connected to a battery. As an alternative to wire connections, detonation of the charge may be by a radio signal to a power source contained within the package as is known in the art Both the excitation of the structure and the response of the structure are measured by standard instruments known in the art, for example, those manufactured by MLI (Manufacturing Laboratories, Inc.) or any other suitable device(s). The units of excitation are any units of force (e.g., Newtons, pound, and the like). Typically the measurement of the response is in displacement (e.g., meters, millimeters, inches), velocity (e.g., meters/second or inches/second), or acceleration (e.g., meters/sec/sec or inches/sec/sec). Thus, the excitation force is measured with the accelerometer and knowledge of the accelerometer mass, and the data is collected by a data acquisition system such as is made by MLI. The response is measured using the accelerometer, a velocity transducer, and a displacement transducer, and the data collected with the data acquisition system.

What is measured is a Frequency Response Function (FRF), which indicates the dynamic characteristics of a structure, and thus, the device could be used in every situation where FRF's are measured. The FRF is computed based on measured excitation and measured response to that excitation by methods known in the art. The pulse excitation excites a broad range of frequencies simultaneously. For small end mills in machine tools, the bandwidth of about 3000 Hertz (Hz) is generally appropriate, whereas with large structures such as bridges, a bandwidth on the order of about 100 Hz is useful. For each potential application of the invention herein, there is a different frequency range of interest, and the excitation is to be tailored to that application. For commercial sales of such products, the bandwidth may be specified on the packaged device.

The device herein may be made to be disposable by utilizing mass-produced, microelectronic accelerometers such as those found in airbag systems. Use of microelectronics mechanical systems (MEMS) transducers, produced similarly to the production of mechanical devices such as computer chips, has the potential to make this process very inexpensive.

Figure 2:
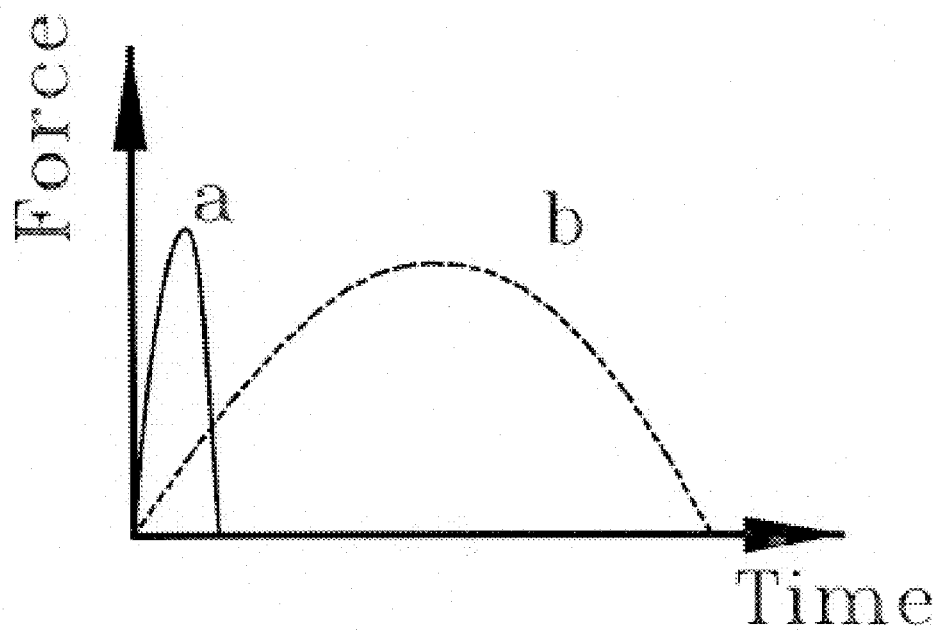
FIG. 2 is a graph of Force vs. Time for prior art hammers. The solid line a is for a hammer with a small mass and a stiff tip, and dashed line b is for a hammer with a large mass and a soft tip.
Figure 3:
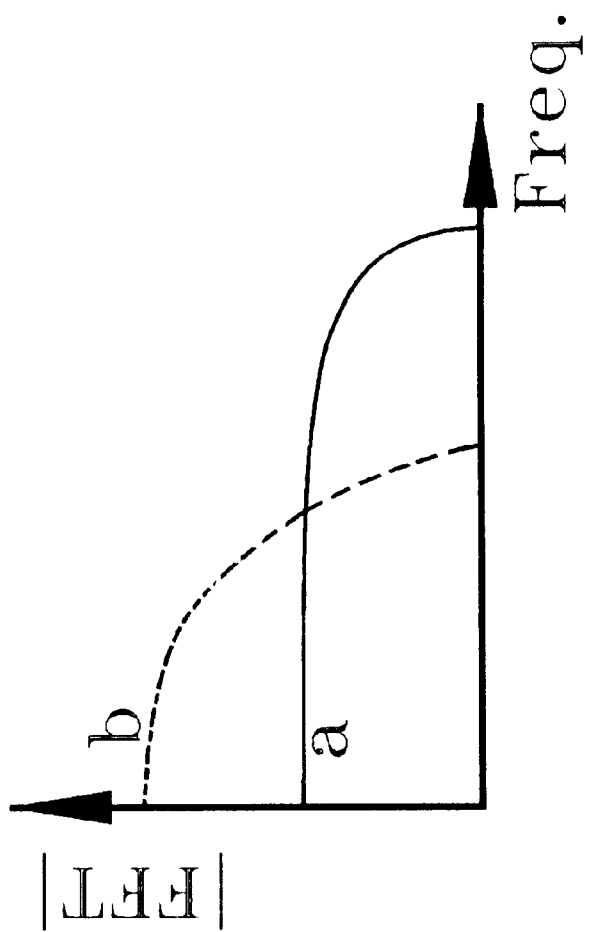
FIG. 3 is a graph of Fast Fourier Transform (FFT) vs. Frequency for the two hammers shown in FIG. 2.

Testing of a device according to the invention and comparison to tests with a hammer device known in the art shows that the device functions properly for its intended purpose. Before showing the results seen with the invention, it is informative to review the type of results seen with previously known hammers. FIG. 2 shows the impact forces produced by two different prior art hammers ("a" has a small mass and a stiff tip; and "b" has a large mass and a soft tip). The selection of the hammer is dictated by the expected dynamic characteristics of the structure, as is further described in FIG. 3. FIG. 3 shows the results of calculation of time domain signals into frequency domain signals using the Fast Fourier Transform technique as is known in the art. This plot shows the amplitudes of sinusoidal signals of different frequencies, which if added together would produce the time signal shown in FIG. 2. These results for the prior hammers, show that the hammer impact which is short in time produces a narrow bandwidth. Therefore, the wide-bandwidth requirement of testing dictates a small hammer with a stiff tip as shown in "a" in these two figures; however, it is difficult to hit the structure hard with such a small hammer. The high force requirement would suggest a more massive hammer, but this leads to unacceptably bandwidth, as shown in "b". Neither type of prior hammer provides a controlled, broad bandwidth, high force excitation to a structure.

FIGS. 4–8 show that the device of the invention can duplicate the results of traditional impact testing, but offers important improvements over the prior hammers. FIGS. 4a–4b show the time measurement made during a hammer impact test with a prior hammer, while FIGS. 5a–5b show analogous results made with the device of the invention. By measuring the acceleration of the separated accelerometer, and by knowing its mass, the force acting on the target was calculated, and the results of that calculation are presented in FIG. 5a. It can note from this figure that the force imparted to the structure is larger than that imparted with the hammer (shown in FIG. 4a). These measurements were made on a target where traditional impact testing and the method of the invention are both acceptable so that a satisfactory result could be obtained with the prior hammer.

Figure 4A:
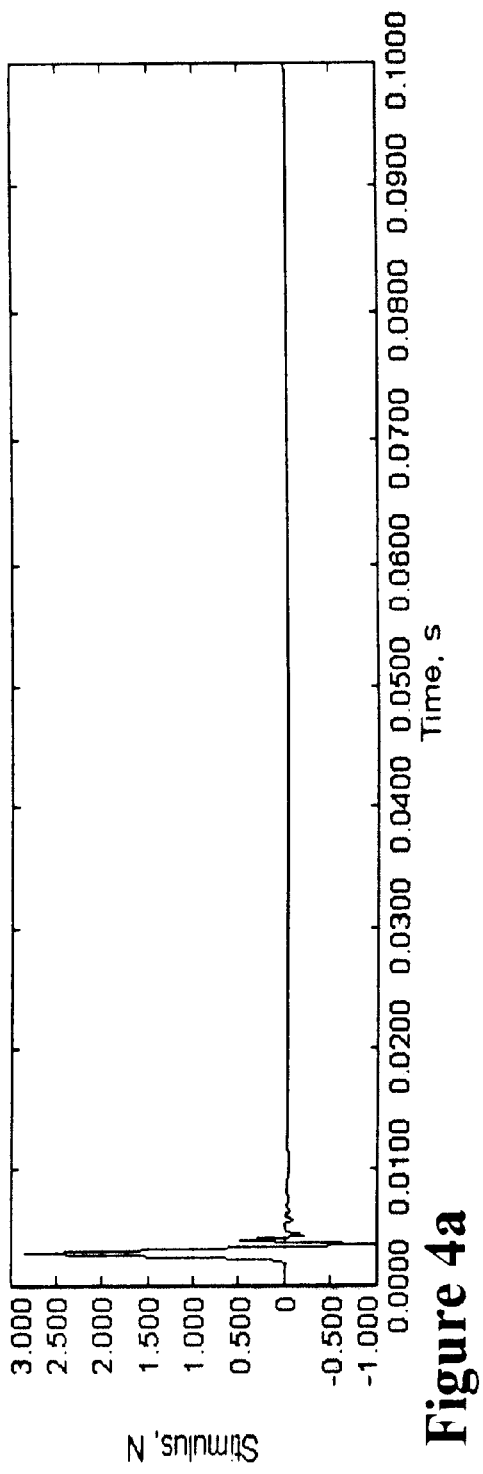
FIGS. 4a and 4b show the Time Display of a prior art hammer on a particular structure.
Figure 4B:
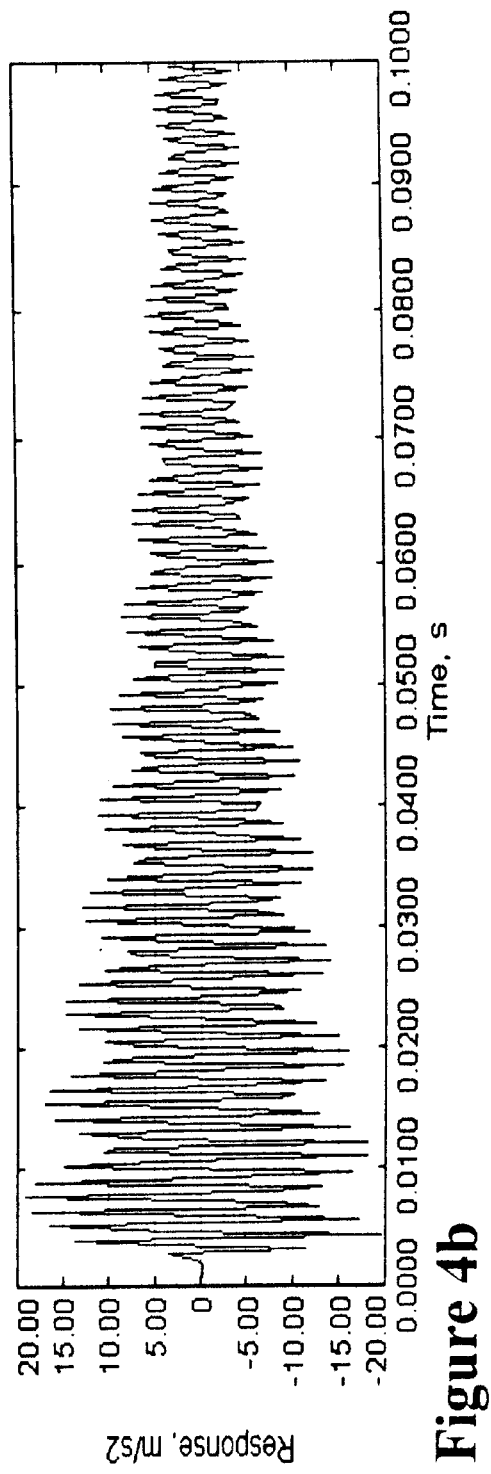
Figure 5A:
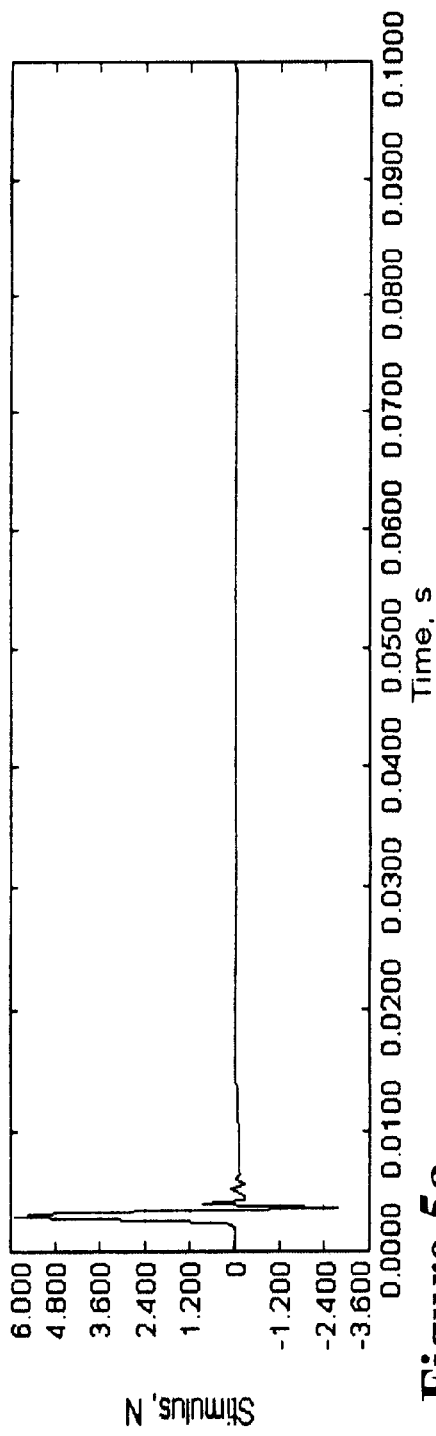
FIGS. 5a and 5b show the Time Display of the device of the invention tested on the same structure as in FIGS. 4a–4b, with FIG. 5a showing hammer force with time, and FIG. 5b showing measured acceleration with time as in FIGS. 4a–4b.
Figure 5B:
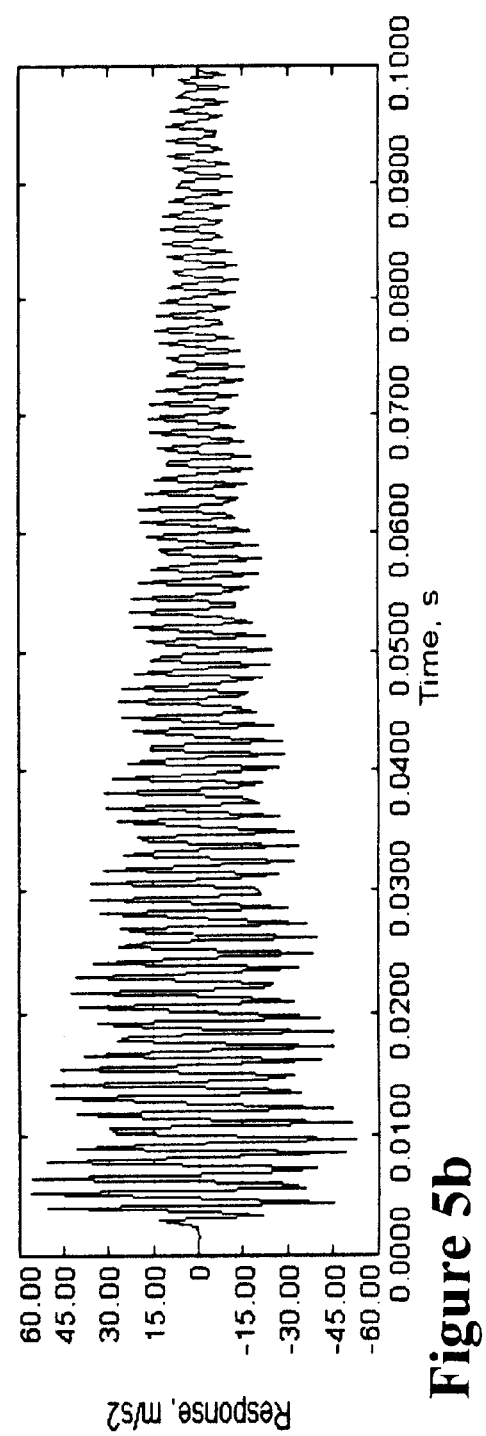
Figure 6A:
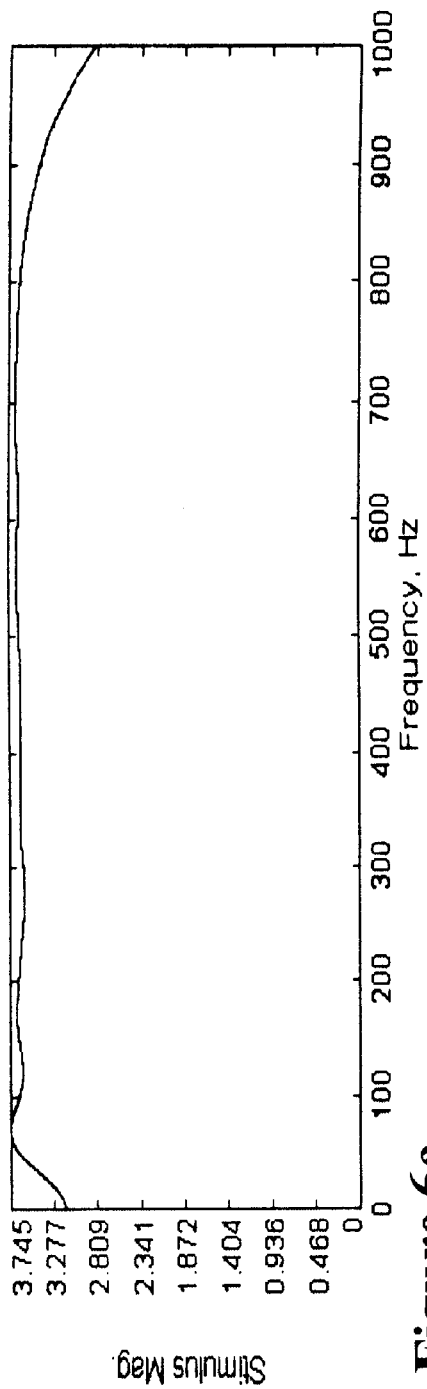
FIGS. 6a–6b show a Spectrum Display of the hammer test of FIGS. 4a–4b, with FIG. 6a showing the magnitude, Mag, which is essentially the same as FFT in FIG. 4a, FIG. 6b shows the frequencies contained in the measured acceleration of the target.
Figure 6B:
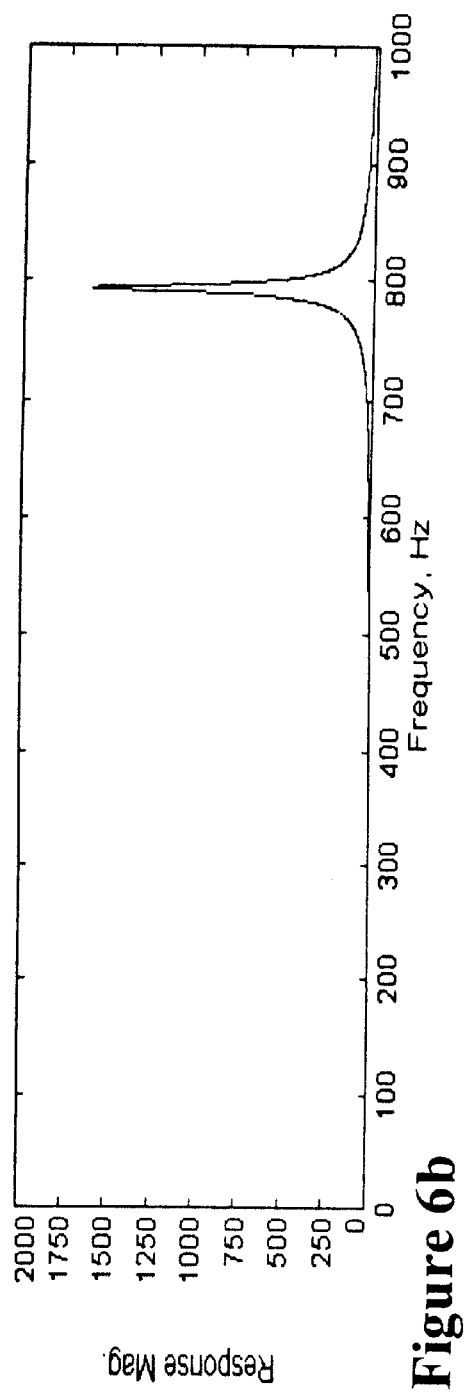

FIGS. 6a–6b show the same data as in FIGS. 4a–4b for the prior hammer, except in the frequency domain. FIG. 6a shows the "bandwidth" of the exciting hammer impact (the "size" of the force at each frequency), and shows that this impact excited frequencies in the range of 0 to 1000 Hz with nearly the same force level. FIG. 6b shows that in the response to the hammer blow (the "size" of the resulting target vibration at each frequency), the target vibrated mostly at about 800 Hz, which is a measurement of the frequency at which the target naturally prefers to vibrate.

Figure 7A:
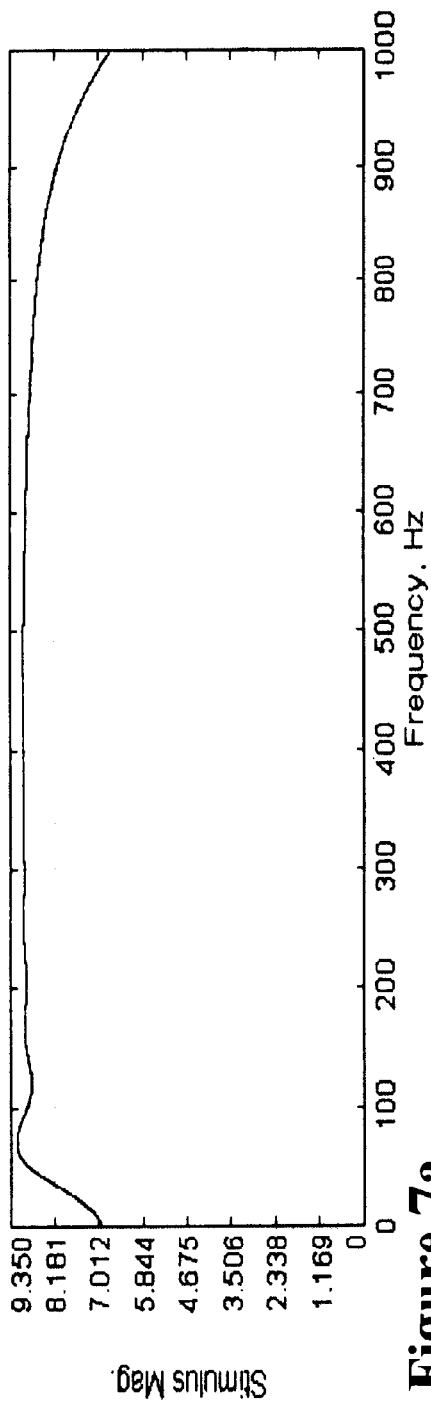
FIGS. 7a–7b show a Spectrum Display of the invention test of FIG. 5, with the same type of plots as shown in FIG. 6a–6b.
Figure 7B:
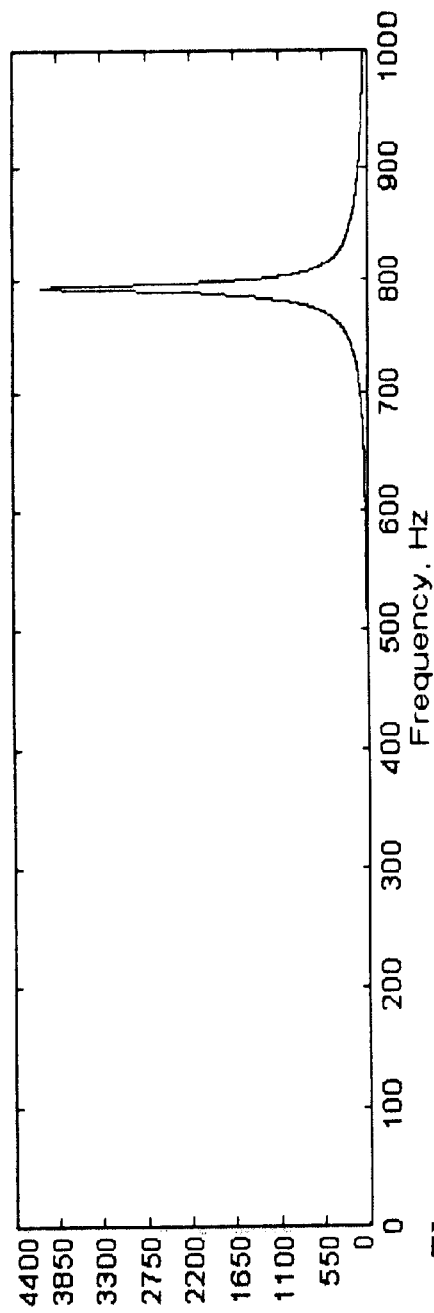

FIGS. 7a–7b show that when the device of the invention is monitored as was done with the prior hammer in FIGS. 6a–6b, there is a bandwidth which was as wide as with the traditional hammer method, and the target was excited in the same way. However, it can be seen that the force level of the excitation was higher with the device of the invention, and that the amplitude of the resulting vibration of the target was higher.

Figure 8A:
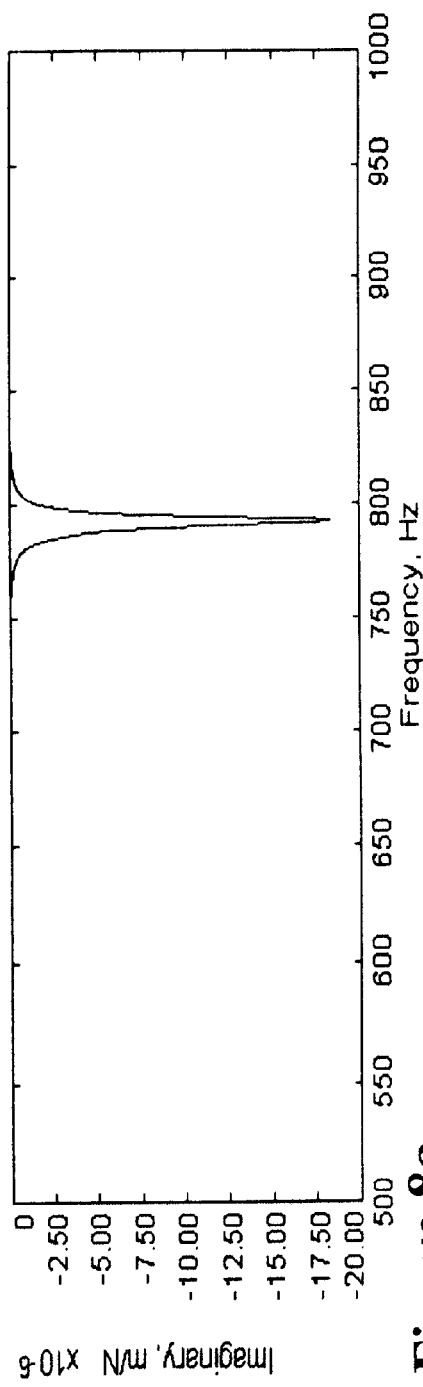
FIGS. 8a–8b show a frequency response function (FRF) plot for the hammer test of FIGS. 4a–4b, showing the measured vibration of the target divided by the measured force from the hammer, both in the frequency domain. The vertical scale is in meters/Newton, and the horizontal scale is in Hertz.
Figure 8B:
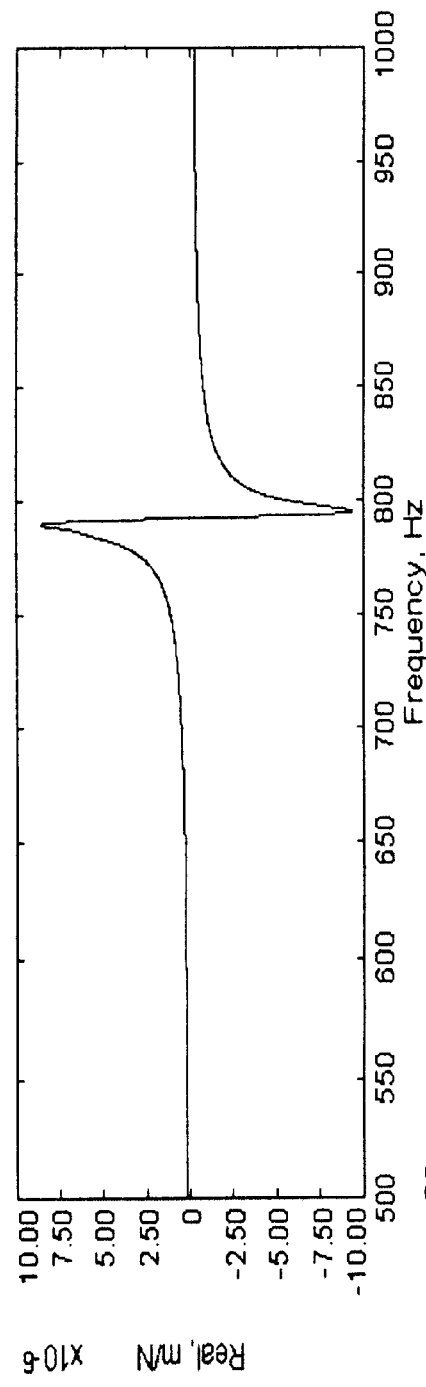

FIGS. 8a–8b show the frequency response function (FRF) from the prior hammer test. This measured vibration of the target divided by the measured force from the hammer, in the frequency domain, results in "real" and "imaginary" parts (the parts of the relationship between displacement and force that are a real number, and a complex number involving the square root of −1, respectively). This measurement allows the calculation of the natural frequency, and of the mass, stiffness and damping of the target, and also allows, for example, the prediction of the cutting performance of a tool. These figures show the dynamic characteristics of the target, obtained by exciting the system with a broad range of frequencies, and then measuring which frequencies got through and at what level.

Figure 9A:
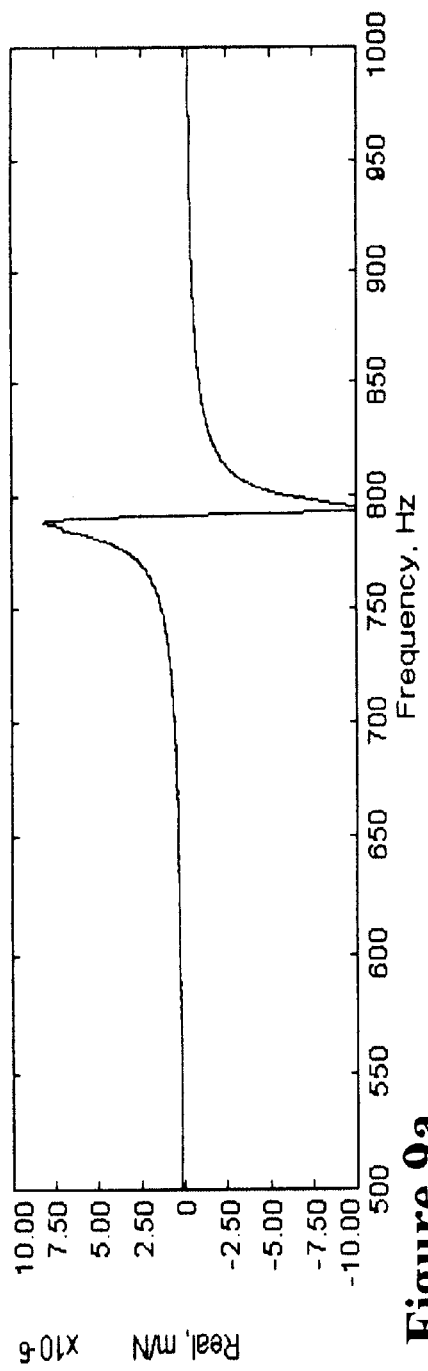
FIGS. 9a–9b is an FRF plot of the invention test of FIG. 5, with two plots, the upper (FIG. 9a) of Real, m/N, and the bottom (FIG. 9b) of Imaginary, m/N (both×10$^{-6}$) each vs. Frequency, Hz.
Figure 9B:
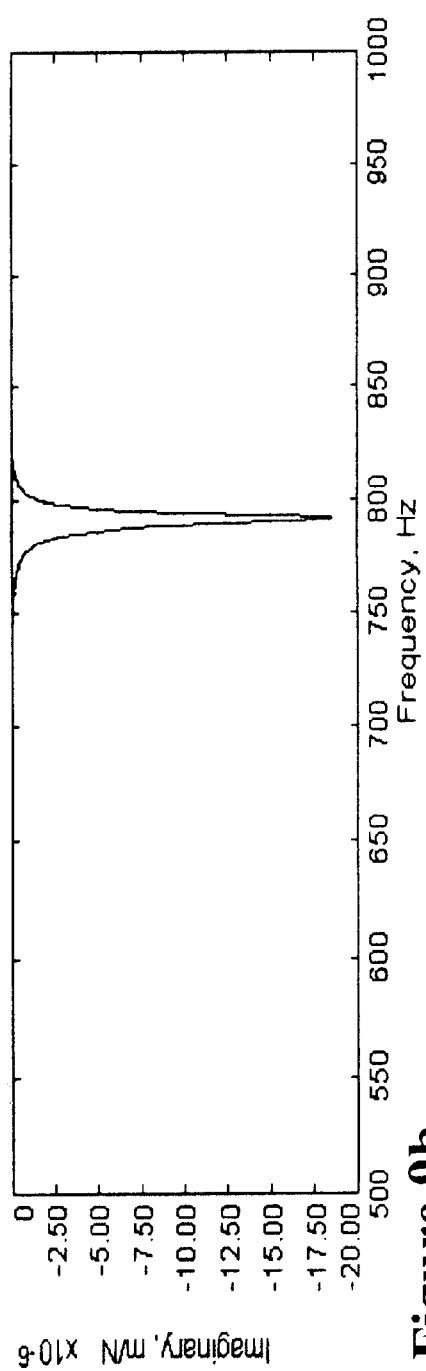

FIGS. 9a–9b show data analogous to that shown in FIGS. 8a–8b, for the device of the invention. FIGS. 9a–9b, which are essentially identical to FIGS. 8a–8b, show that the device of the invention works properly, and as is useful for function in structural testing.

In sum, the figures show that the method and device of the invention herein can provide an excitation pulse which is larger than the pulse produced by a prior art hammer without changing the required performance, as shown by the FRF results.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. A device for exciting a structure during dynamic measurements comprising:
   a) an accelerometer having a known mass;
   b) an explosive charge positioned adjacent the accelerometer;
   c) an ignition means;
   d) means for measuring acceleration of said accelerometer; and
   e) a data acquisition system using data for the acceleration of the accelerometer and for the mass of the accelerometer to calculate an excitation force on the structure, wherein the accelerometer is placed adjacent to the structure at a location on the structure to be tested and the explosive charge is ignited to excite the structure during dynamic measurements, the accelerometer is blown away form the structure.

2. The device according to claim 1, further comprising a data acquisition system.

3. The device according to claim 1, wherein the accelerometer is attached to the explosive charge.

4. A method for exciting a structure during dynamic measurements, comprising the steps of:
   a) providing a device comprising:
      i) an accelerometer having a known mass;
      ii) an explosive charge positioned adjacent the accelerometer;
      iii) an ignition means; and
      iv) means for measuring acceleration of said accelerometer, wherein when the explosive charge is ignited, the accelerometer is blown away from the structure;
   b) placing the accelerometer adjacent the structure at a location on the structure to be tested for exciting the structure curing dynamic measurements;
   c) igniting the explosive charge so that the accelerometer is blown away from the structure; and
   d) providing a data acquisition system using data for the accelerometer and of the mass of the accelerometer to calculate an excitation force on the structure.

5. The method according to claim 4, further comprising providing a data acquisition system, and calculating an excitation force on the structure using knowledge of the acceleration of the accelerometer and of the mass of the accelerometer.

* * * * *